(12) United States Patent
Trerotola

(10) Patent No.: US 7,108,704 B2
(45) Date of Patent: *Sep. 19, 2006

(54) PERCUTANEOUS MECHANICAL FRAGMENTATION CATHETER SYSTEM

(75) Inventor: Scott O. Trerotola, Indianapolis, IN (US)

(73) Assignee: Johns Hopkins University, Baltimore, MD (US)

( * ) Notice: Subject to any disclaimer, the term of this patent is extended or adjusted under 35 U.S.C. 154(b) by 146 days.

This patent is subject to a terminal disclaimer.

(21) Appl. No.: 10/960,773

(22) Filed: Oct. 7, 2004

(65) Prior Publication Data

US 2005/0125016 A1    Jun. 9, 2005

Related U.S. Application Data

(63) Continuation of application No. 10/309,323, filed on Dec. 3, 2002, now Pat. No. 6,824,551, which is a continuation of application No. 09/057,273, filed on Apr. 8, 1998, now abandoned, which is a continuation of application No. 08/609,070, filed on Feb. 29, 1996, now Pat. No. 5,766,191, which is a continuation-in-part of application No. 07/864,714, filed on Apr. 7, 1992, now abandoned.

(51) Int. Cl.
*A61B 17/22* (2006.01)
*A61B 6/00* (2006.01)

(52) U.S. Cl. .................. 606/159; 606/180; 604/508

(58) Field of Classification Search ................. None
See application file for complete search history.

(56) References Cited

U.S. PATENT DOCUMENTS

| 1,167,014 A | 1/1916 | O'Brien |
|---|---|---|
| 2,703,101 A | 3/1955 | Cantwell |
| 2,816,552 A | 12/1957 | Hoffman |
| 3,568,677 A | 3/1971 | Nolan et al. |
| 3,730,185 A | 5/1973 | Cook et al. |
| 3,741,214 A | 6/1973 | Tillander |
| 4,046,150 A | 9/1977 | Schwartz et al. |
| 4,273,128 A | 6/1981 | Lary |
| 4,417,886 A | 11/1983 | Frankhouser et al. |
| 4,643,186 A | 2/1987 | Rosen et al. |
| 4,646,736 A | 3/1987 | Auth |
| 4,650,466 A | 3/1987 | Luther |
| 4,655,217 A | 4/1987 | Reed |

(Continued)

FOREIGN PATENT DOCUMENTS

DE    33 40 581 C1    6/1985

(Continued)

OTHER PUBLICATIONS

Schmitz-Rode, "New Device for Percutaneous . . . Emboli", Radiology, 1991; 180, pp. 135-137.

(Continued)

*Primary Examiner*—Glenn K. Dawson
(74) *Attorney, Agent, or Firm*—Amster, Rothstein & Ebenstein LLP

(57) ABSTRACT

A percutaneous thrombolytic device, also referred to herein as a percutaneous mechanical fragmentation catheter system, that includes a wire cage or basket attached to a rotational drive motor. The fragmentation basket, ensheathed in an outer catheter, is introduced into the clotted graft or vessel via an introducer sheath. When deployed, the basket will automatically conform to the inner dimensions of the vessel lumen. The rotating basket is slowly withdrawn through the clotted graft, mechanically fragmenting the clot. The fragmented, homogenized debris can be flushed into the venous system or aspirated.

52 Claims, 11 Drawing Sheets

U.S. PATENT DOCUMENTS

| | | | |
|---|---|---|---|
| 4,696,667 A | 9/1987 | Masch |
| 4,706,671 A | 11/1987 | Weinrib |
| 4,747,406 A | 5/1988 | Nash |
| 4,772,258 A | 9/1988 | Marangoni et al. |
| 4,790,812 A | 12/1988 | Hawkins, Jr. et al. |
| 4,857,045 A | 8/1989 | Rydell |
| 4,885,003 A | 12/1989 | Hillstead |
| 4,886,061 A | 12/1989 | Fischell |
| 4,895,560 A | 1/1990 | Papantonakos |
| 4,909,781 A | 3/1990 | Husted |
| 4,919,133 A | 4/1990 | Chiang |
| 4,921,484 A | 5/1990 | Hillstead |
| 4,923,462 A | 5/1990 | Stevens |
| 4,926,858 A | 5/1990 | Gifford |
| 4,936,845 A | 6/1990 | Stevens |
| 4,950,277 A | 8/1990 | Farr |
| 4,957,482 A | 9/1990 | Shiber |
| 4,966,604 A | 10/1990 | Reiss |
| 5,011,490 A | 4/1991 | Fischell et al. |
| 5,019,088 A | 5/1991 | Farr |
| 5,026,384 A | 6/1991 | Farr et al. |
| 5,030,201 A | 7/1991 | Palestrant |
| 5,034,001 A | 7/1991 | Garrison |
| 5,049,154 A | 9/1991 | Quadri |
| 5,053,044 A | 10/1991 | Mueller et al. |
| 5,069,679 A | 12/1991 | Taheri |
| 5,071,424 A | 12/1991 | Reger |
| 5,100,423 A | 3/1992 | Fearnot |
| 5,100,425 A | 3/1992 | Fischell et al. |
| 5,133,725 A | 7/1992 | Quadri |
| 5,154,724 A | 10/1992 | Andrews |
| 5,158,564 A * | 10/1992 | Schnepp-Pesch et al. ... 606/159 |
| 5,176,693 A | 1/1993 | Pannek |
| 5,192,291 A | 3/1993 | Pannek |
| 5,195,954 A | 3/1993 | Schnepp-Pesch et al. |
| 5,224,945 A | 7/1993 | Pannek, Jr. |
| 5,246,426 A | 9/1993 | Lewis et al. |
| 5,269,751 A | 12/1993 | Kaliman et al. |
| 5,282,484 A | 2/1994 | Reger |
| 5,308,354 A | 5/1994 | Zacca et al. |
| 5,409,454 A | 4/1995 | Fischell et al. |
| 5,490,859 A | 2/1996 | Mische et al. |
| 5,628,746 A | 5/1997 | Clayman |
| 5,728,129 A | 3/1998 | Summers |
| 5,766,191 A * | 6/1998 | Trerotola ............... 606/159 |
| RE36,764 E | 7/2000 | Zacca et al. |
| 6,165,187 A | 12/2000 | Reger |
| 6,824,551 B1 * | 11/2004 | Trerotola ............... 606/159 |

FOREIGN PATENT DOCUMENTS

| | | |
|---|---|---|
| DE | 34 00 416 A1 | 7/1985 |
| DE | 35 01 707 A1 | 7/1986 |
| DE | 35 25 458 A1 | 1/1987 |
| DE | 37 17 657 A1 | 12/1988 |
| DE | 37 17 658 A1 | 12/1988 |
| DE | 3732236 | 12/1988 |
| DE | 39 13 935 A1 | 10/1990 |
| DE | 39 13 936 A1 | 10/1990 |
| DE | 40 04 507 A1 | 8/1991 |
| DE | 40 25 799 A1 | 2/1992 |
| DE | 40 38 206 A1 | 2/1992 |
| EP | 0 117 519 A1 | 9/1984 |
| EP | 0 189 329 A2 | 7/1986 |
| EP | 0229620 | 7/1987 |
| EP | 0 268 228 B1 | 5/1988 |
| EP | 0 337 918 B1 | 10/1989 |
| EP | 0 338 965 B1 | 10/1989 |
| EP | 0 427 429 A2 | 5/1991 |
| EP | 0 428 998 A1 | 5/1991 |
| EP | 0 442 137 B1 | 8/1991 |
| EP | 0 446 020 B1 | 9/1991 |
| EP | 0 472 368 B1 | 2/1992 |
| EP | 0 477 020 B1 | 3/1992 |
| EP | 0533321 | 3/1993 |
| FR | 2 639 237 A1 | 5/1990 |
| WO | WO 88/00069 | 1/1988 |
| WO | WO 90/00371 | 1/1990 |
| WO | 9002523 | 3/1990 |
| WO | WO 91/02494 | 3/1991 |
| WO | WO 92/03098 | 3/1992 |
| WO | WO 93/19679 | 10/1993 |

OTHER PUBLICATIONS

Trerotola, et al, "New Device for Mechanical. . . Grafts", SCVIR Meeting Abstracts, Feb. 1992, vol. 3, No. 1, p. 25.

Trerotola, et al, "Pulmonary Emboli.. Thrombolysis", Radiology, Nov. 1995; p. 318.

Lajvardi et al, "Evaluation of Venous Injury . . . Device", CardioVasc. Intervent. Radiology, Jun. 1, 1995; 18: pp. 178-178.

Trerotola, et al, "Thrombosed Dialysis . . . Urokinase", Intervent. Radiology, Jun. 1994; 191(3): pp. 721-726.

Lassers, et al, "Removal of an Iatrongenic . . . Catcher", Am. Heart. J., Mar. 1967, vol. 73, No. 3, pp. 375-378.

Tanaka, et al, "Nonsurgical Technique . . . Artery", Catheter. and Card. Diagnosis, 1983; 9: pp. 109-112.

Harinck et al, "Atraumatic . . . in Children", European . . . Cardiol., 1974, 1/4: pp. 421-422.

Noe, "Removal of Intravascular . . . Retriever", Urology, Feb. 1981, vol. XVII, No. 2, pp. 184-185.

Lynch, "Retrograde Embolectomy", The Lancet, Apr. 1963, pp. 751-752.

Bildsoe et al, "Mechanical . . . New Concept", Radiology, 1989, 171: pp. 231-233.

Gunther et al, "Minibasket for percutaneous . . . Technical Note", Cardiovas. Intervent. Radiol., 1991: pp. 195-198.

Starck et al, "Percutaneous Aspiration Thromboembolectomy", Interventional Radiology, Jul. 1985, pp. 61-66.

Schmitz-Rode et al, "Percutaneous . . . Systems", Investigate Radiology, Jun. 1991, vol. 26, pp. 557-562.

Greep, et al, "A Combined Technique . . . Embolectomy", Arch Surg. vol. 105, Dec. 1972, pp. 869-874.

Trerotola, So, et al., entitled "Pulmonary emboli from pulse-spray and mechanical thrombolysis: evaluation with an animal dialysis-graft model," Radiology. 1996 Jul.;200(1):169-76.

Trerotola, So, et al., entitled "Percutaneous use of the Forgarty adherent clot catheter," J. Vasc. Interv. Radiol. Jul.-Aug. 1995;6(4):578-80.

Trerotola, So, et al., entitled "Preclinical in vivo testing of a rotational mechanical thrombolytic device," J Vasc Interv Radiol. Sep.-Oct. 1996;7(5):717-23.

Lajvardi, A., et al., entitled "Evaluation of venous injury caused by a percutaneous mechanical thrombolytic device," Cardiovasc Intervent Radiol. May-Jun. 1995; 18(3): 172-8.

Trerotola, So, et al., entitled "Percutaneous Thrombectomy Device: Preliminary Clincal Experience and Follow-up Findings," Presented at the Radiological Society of North American (RSNA) in Chicago, 1992 (Abstract).

Guenther, MD, et al., entitled "Aspiration Catheter for Percutaneous Thrombectomy: Clincal Results," Radiology 1990; 175: 271-273.

Gaylord, GM, et al., entitled "Kensey Catheter Introduction and Safety in Canine Pulmonary Arteries," Radiology, Mar. 1990, vol. 174, No. 3, Part 2, p. 1066.

* cited by examiner

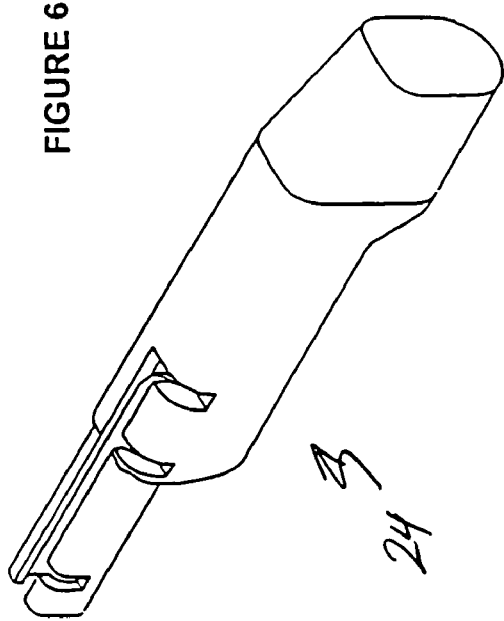
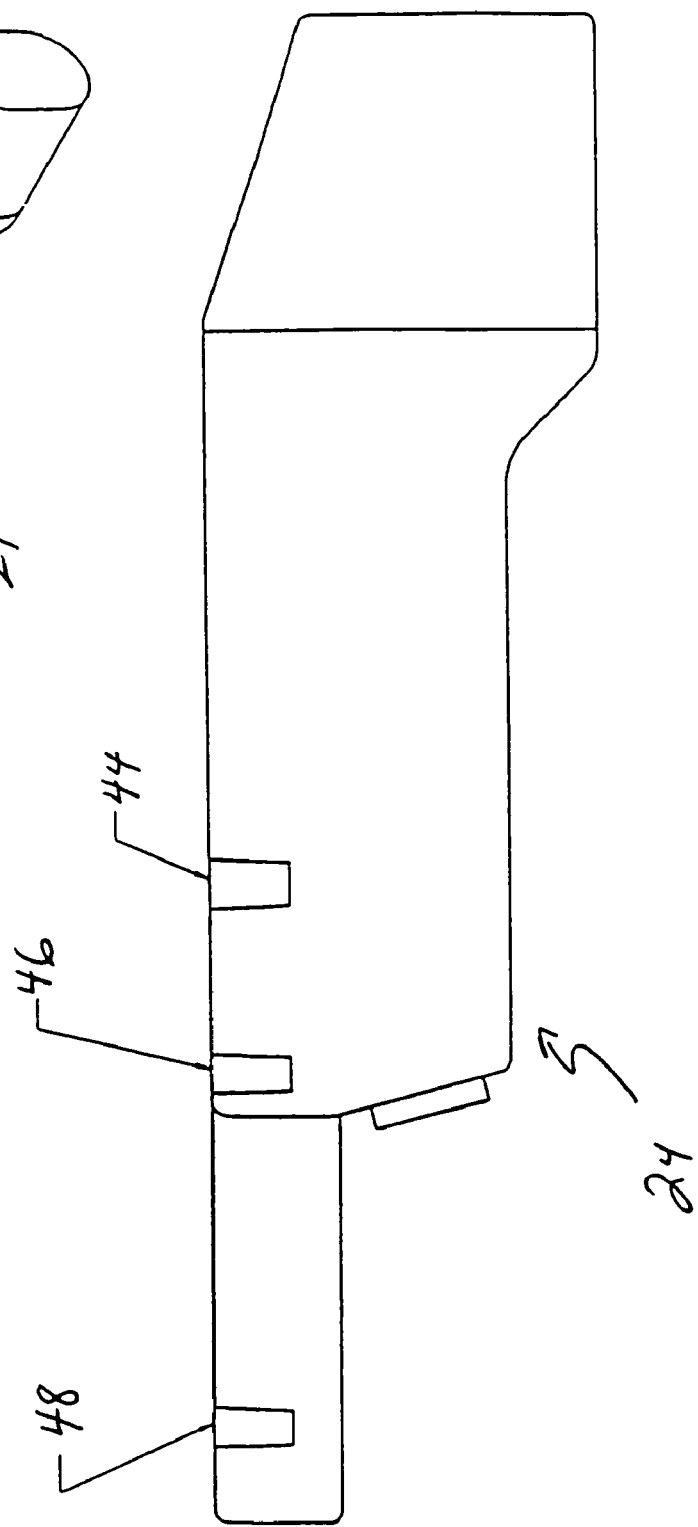

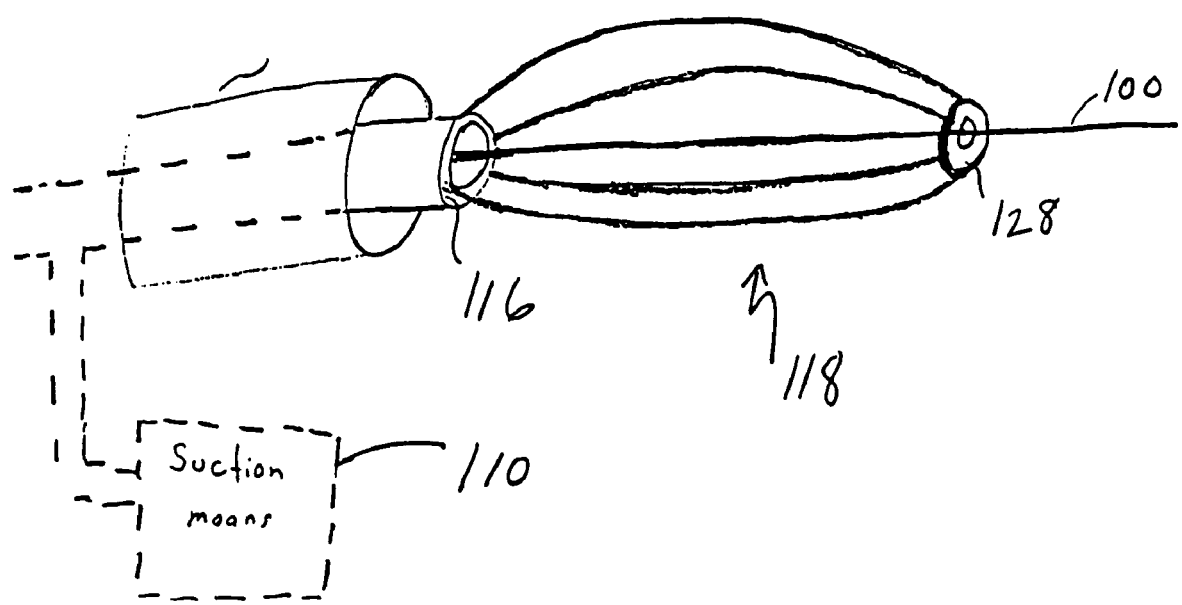

PERCUTANEOUS MECHANICAL FRAGMENTATION CATHETER SYSTEM

This application is a continuation of U.S. patent application Ser. No. 10/309,323, filed Dec. 3, 2002, now U.S. Pat. No. 6,824,551, which is a continuation of U.S. patent application Ser. No. 09/057,273, filed Apr. 8, 1998, now abandoned, which is a continuation of U.S. patent application Ser. No. 08/609,070, filed Feb. 29, 1996, now U.S. Pat. No. 5,766,191, issued Jun. 16, 1998, which is a continuation-in-part of U.S. patent application Ser. No. 07/864,714, filed Apr. 7, 1992, now abandoned, the disclosures of all of which are incorporated herein by reference in their entireties.

BACKGROUND OF THE INVENTION

1. Field of the Invention

The invention relates to the catheter for mechanically fragmenting clots within the vascular system and, in particular, within occluded synthetic vascular grafts. The catheter is used percutaneously thereby obviating invasive surgical procedures. The use of the catheter reduces or eliminates the need for pharmacological clot dissolution.

2. Background Information

Approximately 150,000 patients in the United States are undergoing chronic hemodialysis. A significant problem for these patients is thrombosis of their dialysis access grafts. This contributes greatly to patient morbidity and hospitalization. Various prior art techniques have attempted to break up clots and/or other obstructing materials, such as neointimal hyperplasia in the vascular system and in synthetic grafts. Although surgery has been the traditional management for thrombosed access grafts and fistulae, percutaneous chemical thrombolysis, the use of thrombolytic agents to dissolve clots, is playing an increasingly important role for hemodialysis patients. Currently, the most popular technique is pulse-spray thrombolysis; however, use of thrombolytic agents such as Urokinase or Streptokinase is associated with relatively high costs, prolonged procedure time, and the potential for bleeding complications. Chronic hemodialysis patients experience blockage of the synthetic access graft (the dialysis fistula) approximately 3–4 times a year. Use of thrombolytic agents requires the patient to spend a day in the hospital each time the dialysis fistula occludes. Moreover, pharmacological therapy requires long time commitments for infusion or medical personnel commitments for pulse-spray techniques.

Surgical thrombectomy has also been used to restore access for dialysis and has opened vascular ducts occluded by clots. Again, the expense is excessive because operating room time must be used. Such techniques use a Fogarty balloon catheter in the operating room, although a Fogarty balloon catheter may be used percutaneously.

Various mechanical devices have been developed that are designed to mechanically remove atheromatous plaque; most of these devices are said to remove thrombus material also. Most of these devices cut the material and then collect or remove the resulting debris from the vascular system. Various atherectomy devices are described in the following patents: U.S. Pat. No. 4,957,482 issued to Samuel Shiber; U.S. Pat. No. 4,696,677 issued to Halmut Masch; U.S. Pat. No. 5,034,001 issued to Michi E. Garrison et al.; U.S. Pat. No. 4,950,277 issued to Andrew Farr; U.S. Pat. No. 4,926,858 issued to Hanson Grifford, III, et al.; U.S. Pat. No. 4,886,061 issued to Robert E. Fischell et al.; U.S. Pat. Nos. 4,923,462 and 4,936,845, issued to Robert Stevers et al; and U.S. Pat. No. 4,909,781 issued to Royce Hosted. The above devices share common problems—they require larger sheath size and create a limited channel size. Moreover, the prior art devices do not automatically accommodate to changes in the inner lumen dimensions of the graft or vessel caused by the presence of a thrombus or automatically expand outward toward the vessel or conduit walls as the thrombus is being fragmented.

U.S. Pat. No. 5,030,201 issued to Aubrey Palestrant, typifies the problems associated with prior art mechanical devices. Palestrant teaches a plurality of parallel cutting blades which are contained during transport within a protective sheath. In operation, the device cuts a portion of the obstructing material and then a second means is used to manually expand the parallel cutting blade so that a larger core can be cut in the obstructing material. The Palestrant device relies on the relative movement of coaxial catheters to bow the blades outward. The amount of expansion is totally controlled by the operator and the Palestrant device cannot automatically compensate for changes in the inner lumen as obstructing material is removed. The coaxial structure also requires a large diameter protective sheath.

Various mechanical devices, rather than using rotating members to cut the obstructive material use ureteric stone catcher baskets mounted on a catheter tip to grab and remove thrombotic material. The following articles teach the use of such baskets to grab and remove thrombus: 1) "A Combined Technique for Peripheral Arterial Embolectomy" *Arch Surg/* Vol. 105, December, 1972; 2) "Removal of an iatrogenic foreign body from the aorta by means of ureteric stone catheter" *Am. Heart J.* March, 1967; 3) "Nonsurgical Techniques for Removal of Catheter Fragments From the Pulmonary Artery" *Catheterization and Cardiovascular Diagnosis* 9:109–112 (1983); 4) "Atraumatic retrieval of catheter fragments from the central circulation in children" *European Journal of Cardiology*, 1974, 1/4, 421–422; 5) "Removal of Intravascular Foreign Body with Stone Retriever" *Urology*, February 1981, Vol. XVII, No. 2; 6) "Retrograde Embolectomy" *The Lancet*, Apr. 6, 1963; 7) "Mechanical Clot Dissolution: New Concept" *Radiology*, April 1989, 17/: 231–233; 8) "Mini basket for Percutaneous Embolectomy and Filter Protection Against Distal Embolization: Technical Note" *Cardiovasc Intervent Radial* (1991) 14:195–198; and 9) "Percutaneous Aspiration Thromboembolectomy" *Radiology* July, 1985; 156:61–66.

An article appearing in *Radiology* entitled "New Device for Percutaneous Fragmentation of Pulmonary Emboli" (*Radiology*, 1991; 180:135–137) combines a spinning impeller contained within a stone basket. The stone basket does not rotate and is necessary to center the rotating impeller so that it does not inadvertently cut the vessel wall. The device cannot automatically expand the mechanical fragmentor to accommodate the inner lumen dimensions of the vascular conduit.

SUMMARY OF THE INVENTION

The invention represents a new approach to fragmenting clots within the vascular system and in particular within synthetic vascular grafts. The invention overcomes deficiencies in the prior art by: 1) automatically expanding to conform to the inner lumen dimensions and shape; 2) applying a radial pressure so that the fragmentor automatically expands as the thrombus is fragmented and can eventually press against the walls of the conduit; and 3) using a minimal number and size of components so that the catheter can be deployed through a small introducer sheath.

The percutaneous thrombolytic device, also referred to herein as a percutaneous mechanical fragmentation catheter system, comprised of a stone retrieval basket modified to attach to a rotational drive motor. The catheter is introduced into the clotted graft or vessel via an introducer sheath. When deployed, the basket will automatically conform to the inner dimensions of the vessel lumen. The rotating basket is slowly withdrawn through the clotted graft, mechanically fragmenting the clot. The fragmented, homogenized debris (with particles under 3 mm in diameter with the majority under 1 mm) can be flushed into the venous system or aspirated. The wire cage that makes up the basket contains a designed "springiness" enabling it to self-expand. Thus, the cage can conform to the inner lumen dimensions and shape and apply radial pressure against the thrombus material, thereby expanding to homogenize substantially the entire cross-section of the conduit. As the material homogenizes, the cage automatically expands. The fragmentation catheter can be used percutaneously, thereby obviating surgery. The catheter reduces or eliminates the need for pharmacological clot dissolution. This new catheter offers the advantage of shortening procedure time, decreasing cost and risk, allowing the use of smaller sheath size and automatically accommodating for differences in the vessel inside diameter.

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 6 is an isometric view of a rotator assembly in accordance with an embodiment of the invention;

FIG. 7 is an elevational view of the rotator assembly of FIG. 6;

FIG. 10 is an enlarged view of a second embodiment the fragmentation catheter used in conjunction with a guide wire.

DETAILED DESCRIPTION OF THE PRESENTLY PREFERRED EXEMPLARY EMBODIMENTS

In accordance with the preferred embodiment, the percutaneous thrombolytic device (PTD) is a 5 Fr×46 cm catheter with an expandable, e.g., 9 mm nickel-titanium (nitinol) spiral basket cage. The device is attached to a hand-held, preferably battery-operated, rotary unit which spins the basket at least in excess of about 2,000 rpm. In some environments the basket is rotated at approximately 3,000–4,500 rpm. The basket is placed within the thrombosed graft or vessel and spun to pulverize the clot.

Figure 1:
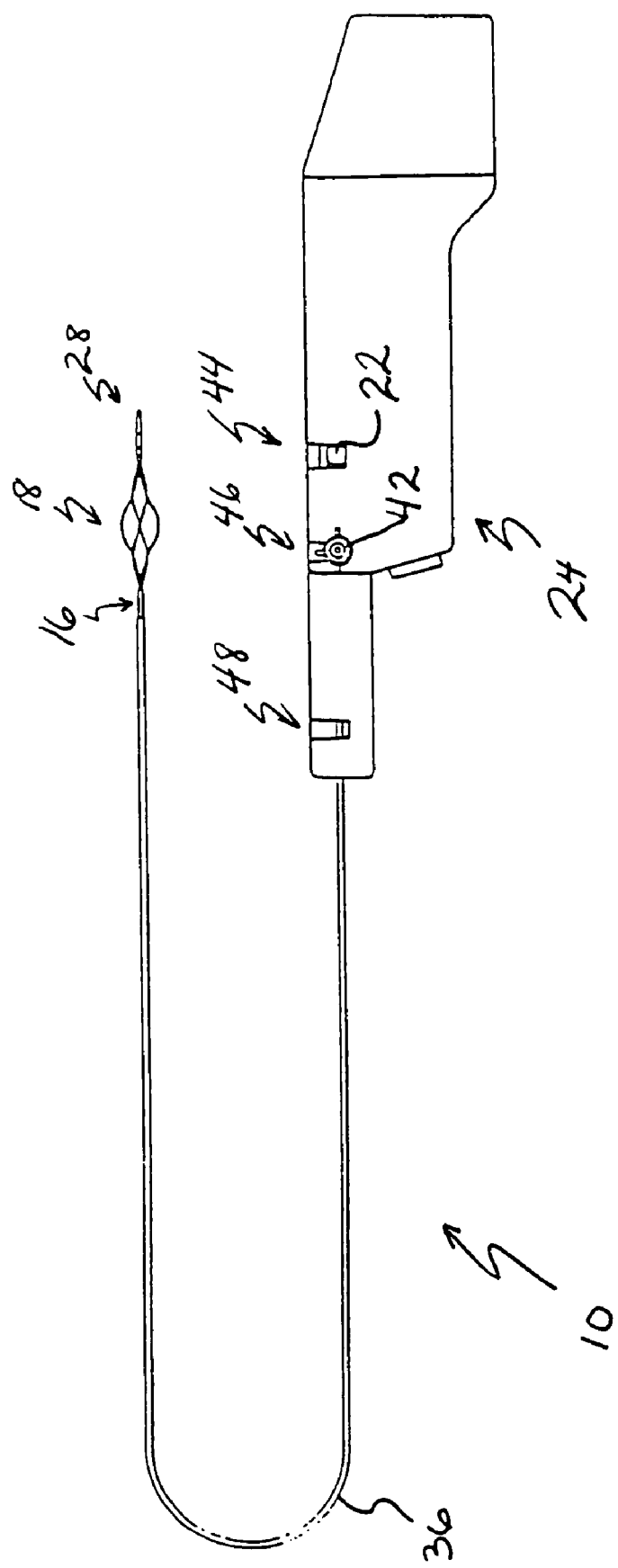
FIG. 1 is a schematic elevational view of a percutaneous mechanical fragmentation catheter system, in accordance with the invention.

FIG. 1 schematically shows the percutaneous mechanical fragmentation catheter system 10 provided in accordance with the present invention. The PTD catheter comprises a torque cable assembly 12 encased within the outer sheath assembly 14.

The torque assembly 12 is made of e.g. a stainless-steel drive cable 16 with a fragmentation basket 18 on the distal end, a splined drive hub 20 on the proximal end, and a cable stop 22 coupled so as to be loosely attached or free spinning as at 21 relative to the torque cable 16 and used to lock the catheter to the rotator unit 24, as detailed below. The original design of the inventive device used a stainless steel spiral basket. However, in accordance with the currently most preferred embodiment, nickel-titanium (nitinol) is used for the wires.

The fragmentation basket or cage 18 is made from three to six wires 26. The wires 26 are flexible and formed with a memory, such that in their normal or relaxed position the wires are bowed and form a basket 18 having a diameter greater than the vascular conduit within which the basket will be used. Because the wires 26 are flexible, the basket 18 may be compressed so that its outer diameter is reduced and conforms to the inner diameter of the vascular conduit. Because the wires 26 are formed with a memory, the wires will cause the basket 18 to seek to expand in size until the wires return to their normal or relaxed position. As such, the fragmentation cage 18 will press against the inner lumen of the vascular conduit and automatically sense and conform to its size and shape. The fragmentation cage 18 can be made of flat or round wire and formed in a straight or helical configuration. Moreover, the wire could have a cutting edge or be impregnated with diamonds or other material, or could be shaped with a cutting edge (e.g. diamond shape) to help fragment the thrombotic material or to enable the device to remove atheroma or neo-intimal hyperplasia. The fragmentation cage 18 should be able to expand from the inner lumen of the outer sheath 36 to fill substantially the entire inner lumen of the vascular conduct. Thus, the wire basket may range in size from, for example, 4.0–30.0 mm depending on the size of the conduit to be treated. Currently, a wire basket diameter of about 6 to 9 mm is most preferred for dialysis fistula.

Figure 2:
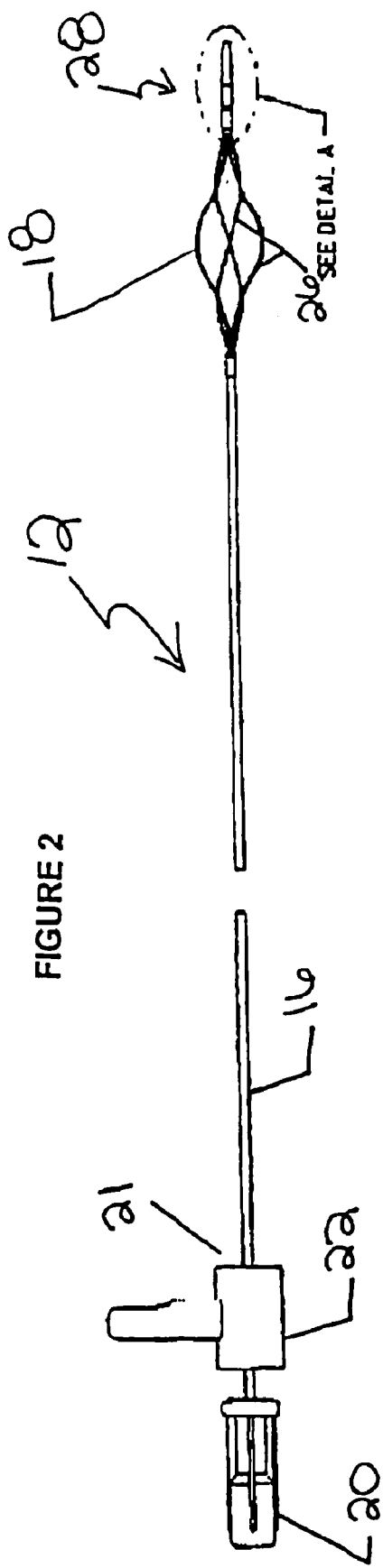
FIG. 2 is a schematic elevational view of a torque cable assembly in accordance with an embodiment of the invention.
Figure 2A:
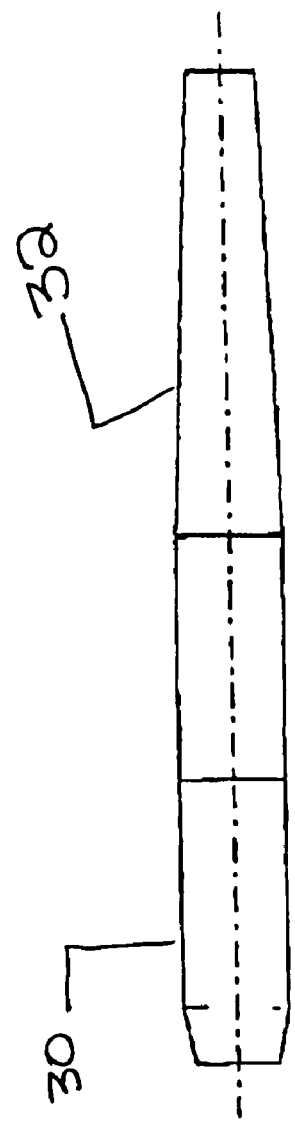
FIG. 2A is a schematic elevational view of detail A in FIG. 2.
Figure 3:
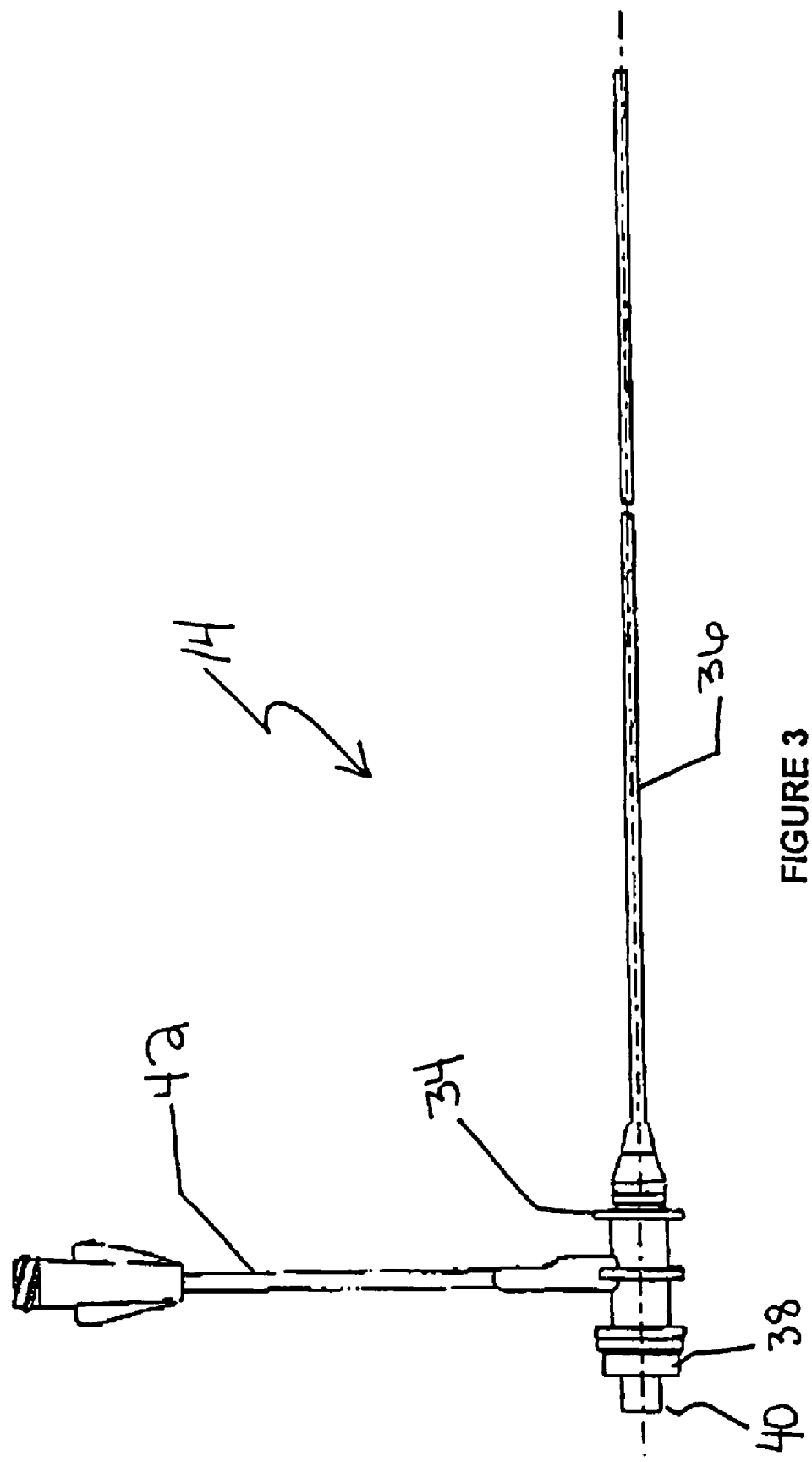
FIG. 3 is a schematic elevational view of an outer sheath assembly in accordance with an embodiment of the invention.

The basket or cage 18 is also preferably designed with a tapered tip 28 on the end to facilitate maneuvering the device through the graft. In the currently preferred embodiment the distal portion of the tip 28 is soft and flexible. Thus, with reference to FIG. 2A, the basket 18 has a metal cap 30 and a soft, flexible plastic tip 32.

The splined drive hub 20 is designed to mate with a splined gear piece (not shown in detail) on the rotator unit 24 in a conventional manner so that as the rotator spins, torque is transmitted along the cable 16 to the fragmentation basket 18. The cable stop 22 locks the torque cable assembly 12 to the rotator unit 24, e.g. by being received in slot 44, so that the two do not separate during use.

The outer sheath assembly 14 comprises a hemostasis hub 34 connected to the outer sheath tubing 36. One can minimize trauma to vascular grafts by using the smallest possible outer sheath 36. The outer sheath could range in diameter from 3 to 9 French. The inventor has found that for dialysis grafts a 4.5–5.0 French outer sheath works very well. The particular length of the outer sheath 36 is variable, but is optimally around 40–50 cm for most procedures.

The hemostasis hub 34 includes a silicone seal 38 and a cap 40 to prevent fluids, such as blood, from contacting the user. A side-arm 42 is also provided for flushing out the lumen before use and/or for injecting contrast during the procedure.

As noted above, a handle or cable stop 22 is provided adjacent the proximal end of the fragmentation assembly 12 to lock the catheter to the rotator unit 24. The side arm 42 of the hemostasis hub 34 likewise is selectively coupled to the rotator unit 24 to define the relative position of the outer sheath 36 and the fragmentation assembly 12. In the illustrated embodiment two relative positions are provided, but additional relative positions can be accommodated.

Figure 5:
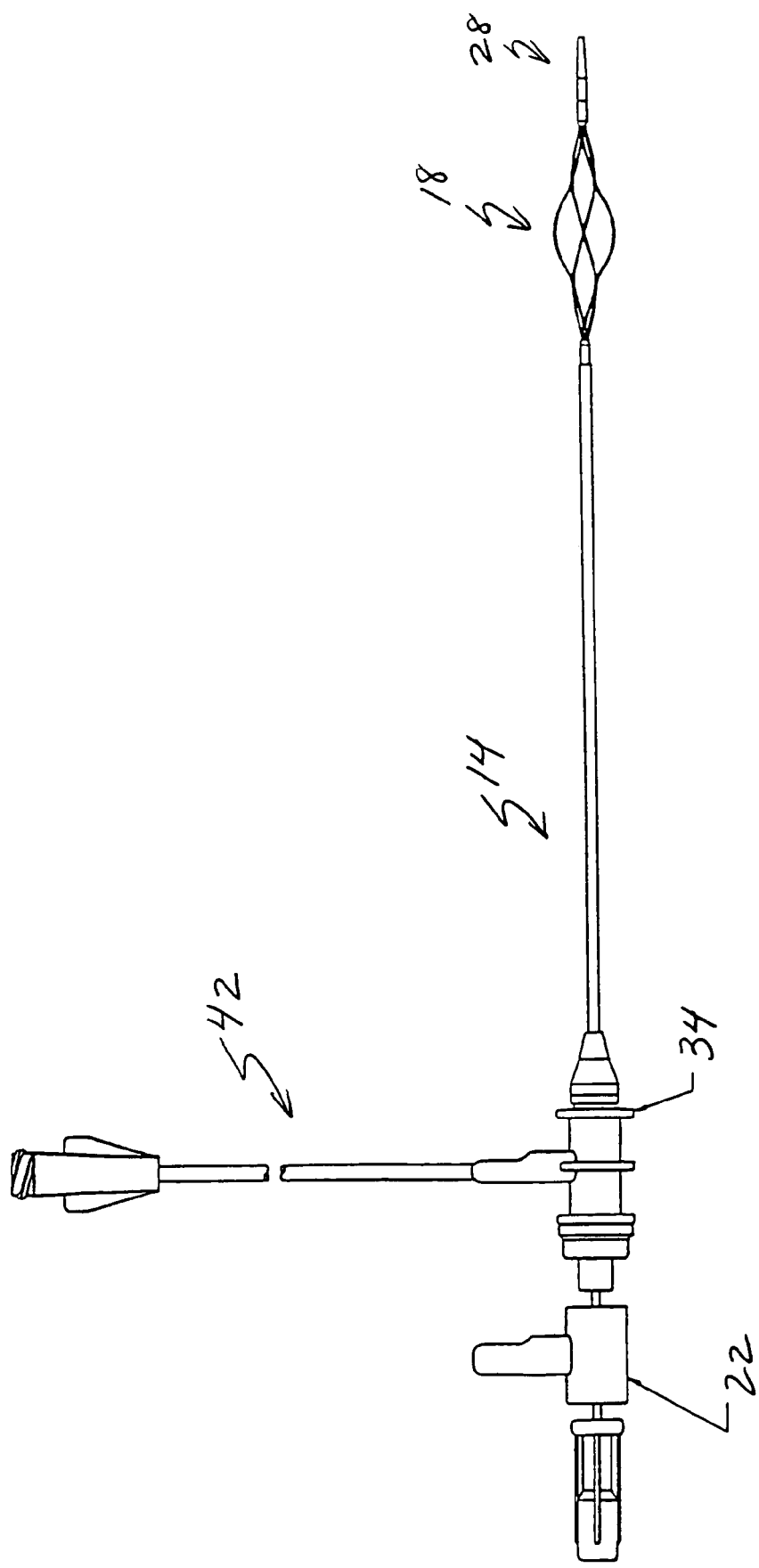
FIG. 5 is a schematic elevational view of a percutaneous thrombolytic device in accordance with the invention, in its deployed position.
Figure 8:
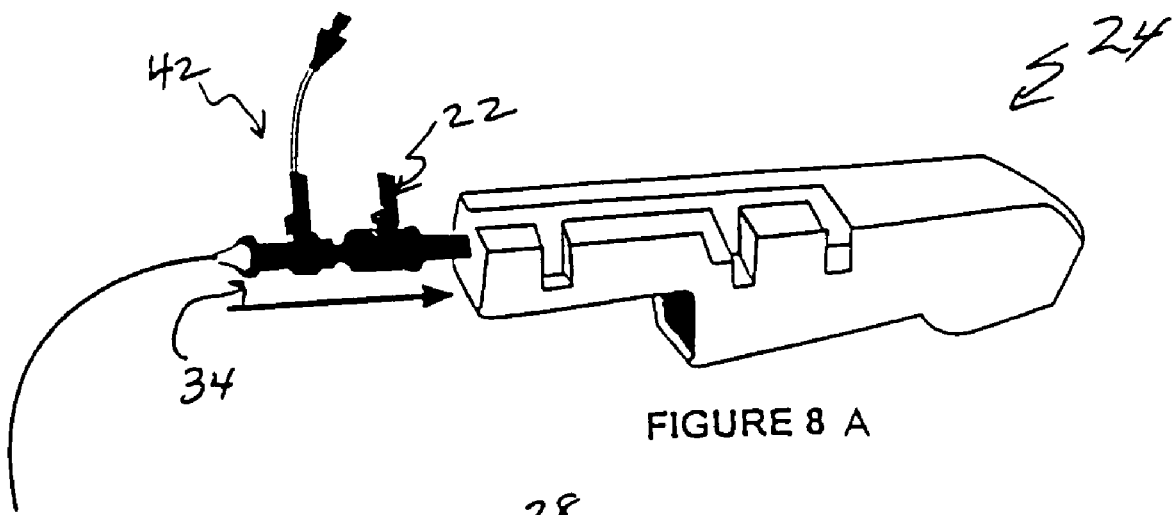
FIG. 8A is a schematic perspective view showing attachment of the percutaneous thrombolytic device to the rotator.
FIG. 8B is a schematic perspective view showing the percutaneous thrombolytic device coupled to the rotator and being disposed in the compressed position.
FIG. 8C is a schematic perspective view showing the percutaneous thrombolytic device coupled to the rotator and being disposed in the deployed position.
Figure 8:
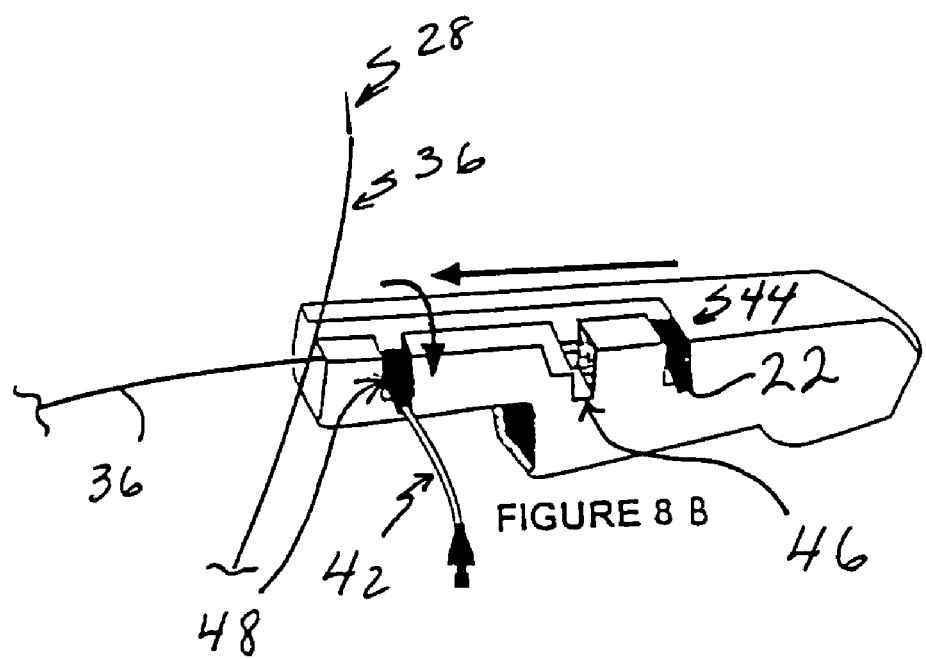
Figure 8:
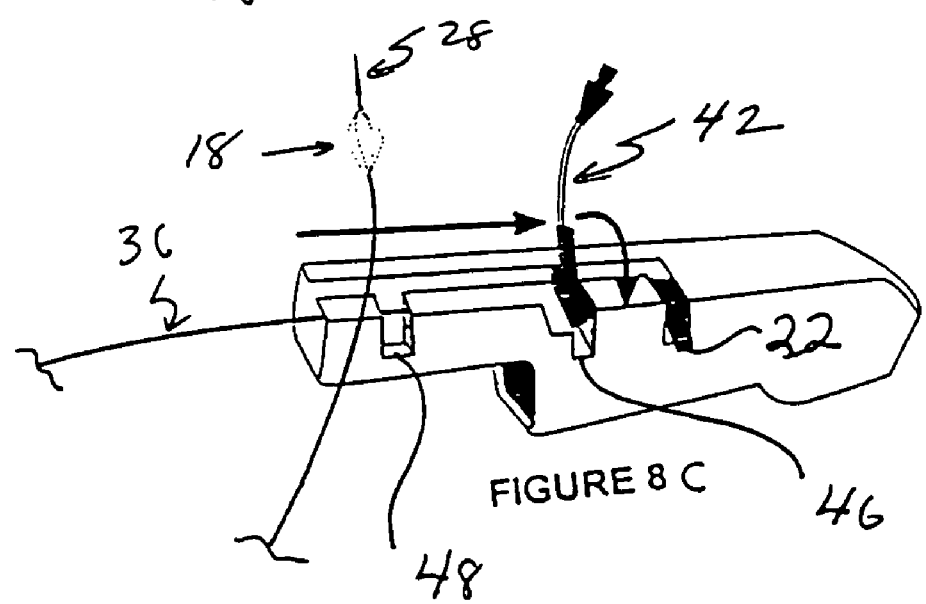
Figure 9:
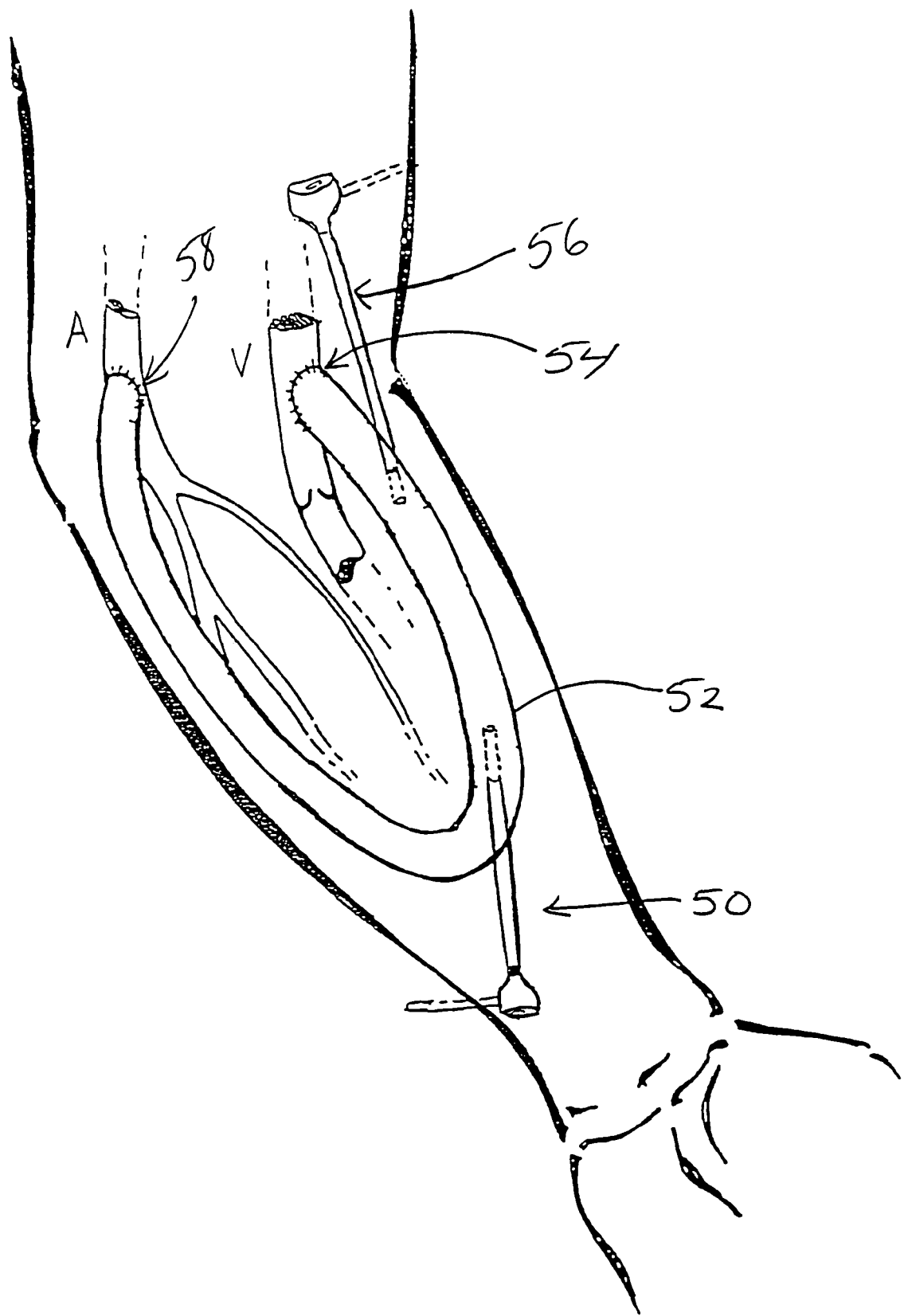
FIG. 9 is a schematic illustration of the placement of arterial and venous sheaths for an exemplary procedure utilizing the device of the invention.

More particularly, with reference to FIGS. 8A–C, movement of side arm 42 away from arm 22 to the lock position defined by slot 48, defines a compressed configuration wherein the fragmentation cage 18 is shielded. On the other hand, movement of side arm 42 toward arm 22 to the lock position defined by slot 46, will expose fragmentation cage 18 thereby defining the deployed configuration of the system. (FIGS. 1 and 5).

Thus, as defined by the relative position of the fragmentation cage and the outer sheath, which is advantageously determined by the configuration of the rotator unit 24, the catheter system has at least two positions, including "compressed" and "deployed". The compressed position is defined as the one in which the basket 18 is within the sheath 36 so that only the plastic distal tip 32 is exposed. This position is used when inserting and maneuvering the catheter within target lumen, whether a graft or vessel. Once the device is positioned appropriately within the target lumen, the "deployed" position is used. This position is obtained when the outer sheath 36 is pulled back relative to the basket thereby exposing the wires 26 and allowing them to expand to the size of the thrombosed lumen for subsequent clot maceration. As can be seen, the provision of arm receiving slots 46, 48 in the rotator unit 24 allows the catheter to lock into either the "deployed" position or the "compressed" position.

By way of example, use of the inventive device to clear a thrombosed graft will be described. In use, in accordance with institutional protocols, an introducer sheath, e.g. a 5 French introducer sheath, is prepared and placed. The "venous" sheath 50 is placed in the venous limb of the graft 52 and directed towards the venous anastomosis 54. Per institutional protocol, any existing central and venous outflow stenoses are assessed. If there is no venous outflow stenosis, a blood pressure cuff is placed on the arm just above the venous anastomosis. If assessment shows the presence of any venous outflow stenosis greater than 10 cm long, any untreatable central venous stenosis/occlusions, or any large pseudoaneurysms, the graft is considered unsalvageable and alternative treatment per institutional protocol should be used.

Figure 4:
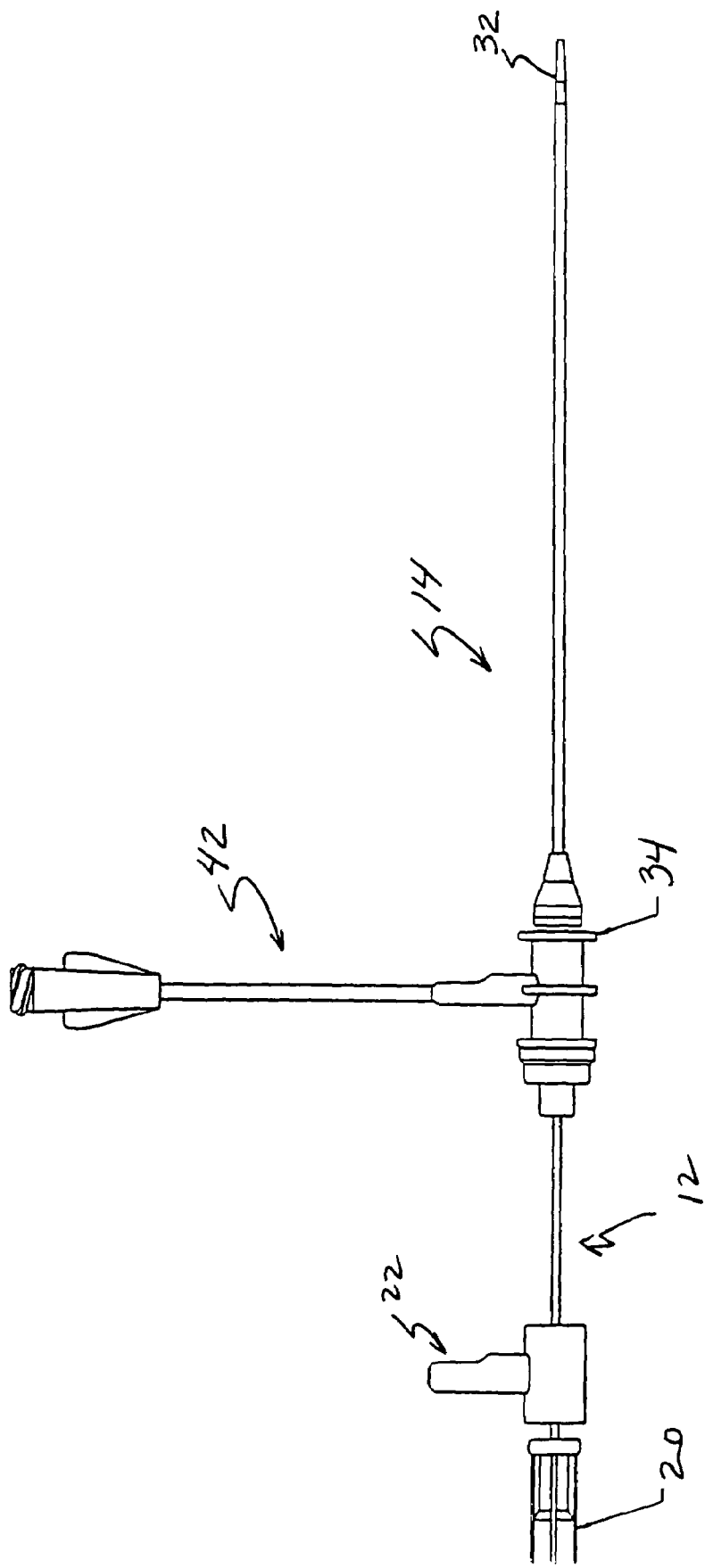
FIG. 4 is a schematic elevational view of a percutaneous thrombolytic device in accordance with the invention, in its compressed position.

If the graft is salvageable, heparin is administered intravenously. Then, the device of the invention is passed in its compressed disposition (FIG. 4) through the venous sheath 50 to the venous limb of the graft 52. The plastic tip on the fragmentation basket is fed up to but not beyond the venous anastomosis 54. The system is then shifted to the deployed position (FIGS. 1 and 5) to expose the fragmentation basket from the outer sheath. The unit is then activated to rotate the fragmentation basket at high speed.

The rotating fragmentation basket is slowly withdrawn along the graft to break up the clot. Once the basket reaches the tip of the access sheath 50 the unit is deactuated to stop rotation. The device is then closed to the compressed position (FIG. 4) and the compressed device is again fed up to but not beyond the venus anastomosis. The basket is then again deployed and rotated to further fragment the clot material. After the appropriate number of passes, e.g., typically, two passes, have been completed, the device is removed from the graft. Approximately 5 cc of the homogenized material is then aspirated and discarded. A small amount of contrast is injected to ensure that adequate thrombolysis of the venous limb has been accomplished.

An introducer sheath, i.e., a 5 French introducer sheath "arterial" 56 is then introduced into the venous limb of the graft 52 and directed towards the arterial anastomosis 58. Using the arterial sheath 56, an appropriate occlusion balloon catheter may be used, i.e. a 5 French Fogarty balloon catheter is passed through the arterial sheath and carefully fed past the arterial anastomosis 58 of the graft 52. The balloon is inflated and the fibrous arterial plug is pulled into the middle of the arterial limb. The occlusion balloon catheter is then deflated and removed.

The compressed device of the invention is then inserted into the arterial limb of the graft via the arterial sheath 56. The plastic tip 32 of the fragmentation catheter is then fed up to but not beyond the arterial anastomosis 58. The device is deployed and actuated to rotate the basket at high speed. The rotating basket is withdrawn through the graft to pulverize the clot. Contrast is used to guide thrombolysis. Once the basket reaches the tip of the access sheath 56 rotation is stopped and the device is placed in its compressed position. The advancement, actuation and withdrawal of the device is then repeated.

After the appropriate number of passes with the device, e.g., typically, two passes, the device is removed and approximately 10 cc of homogenized clot is withdrawn through the arterial sheath and discarded. Contrast is then injected to assess the degree of thrombolysis. Any residual thrombosis is then treated by again using the device of the invention via either sheath as needed. Once thrombolysis is complete, any venous outflow stenosis should be treated by conventional means as dictated by institutional protocol (i.e., PTA balloon atherectomy, etc.). The blood pressure cuff, if used, is then removed and a contrast study of the entire graft is carried out and any further stenosis if indicated is treated per institutional protocol. Finally, the sheaths are removed from the graft and hemostasis is achieved per institutional protocol.

FIG. 10 shows an alternative embodiment for the fragmentation catheter. The fragmentation cage 118 would connect to a hub 128 on its distal end and to a shaft 116 with an inner lumen on its proximal end. A guide wire 100 would be able to pass through the inner lumen of shaft 116 and hub 128. As a result, the guide wire 100 could be positioned in the vascular conduit (not shown) and the fragmentation cage 118 could be controlled by handles (not shown in this embodiment) to be moved along the guide wire 100. An optional suction means 110 could attach to the proximal end of the inner lumen of shaft 116 and draw debris homogenized by the catheter from the vessel.

Figure 11A:
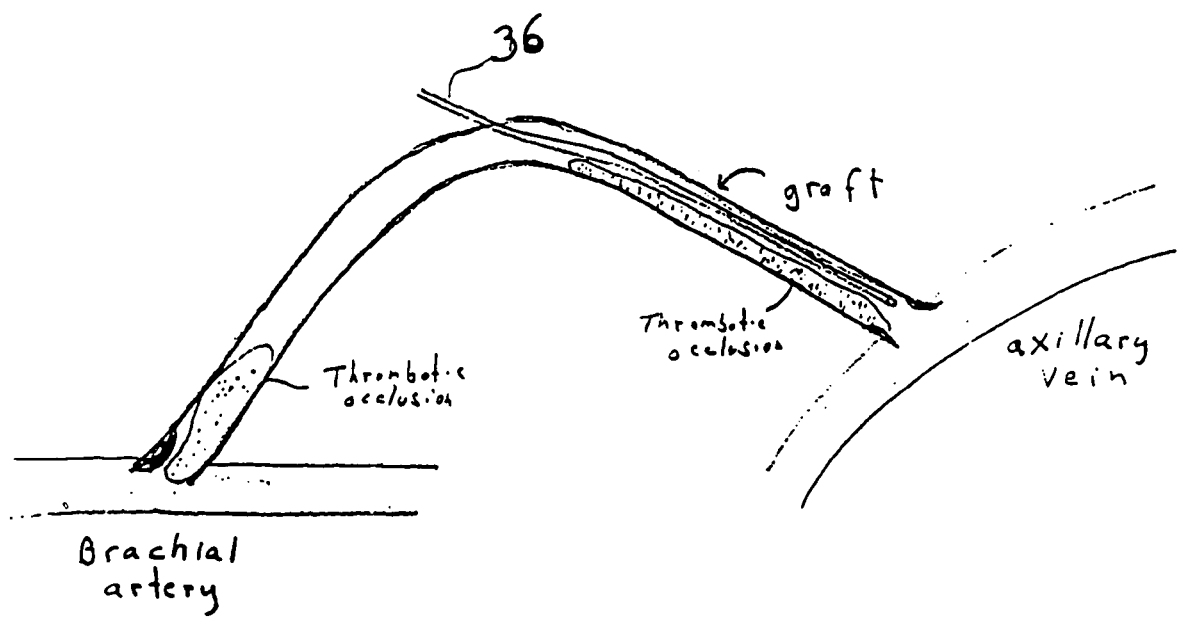
FIGS. 11A, 11B and 11C show the use of the percutaneous mechanical fragmentation catheter system in a dialysis fistula.
Figure 11B:
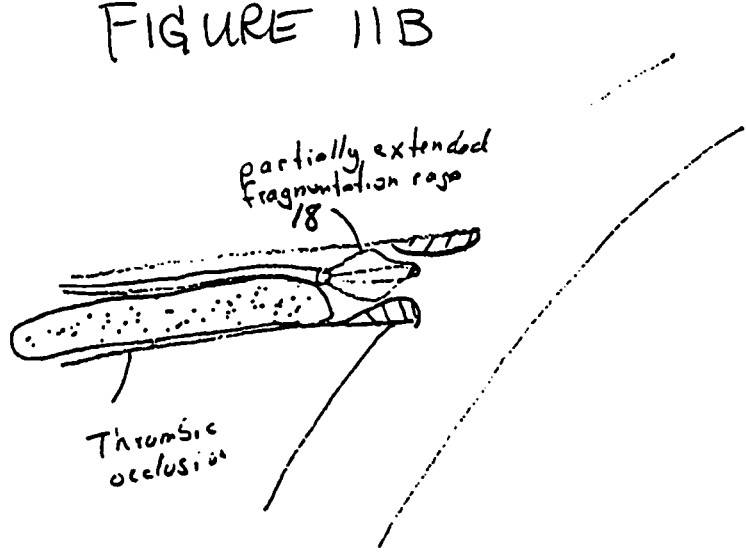
Figure 11C:
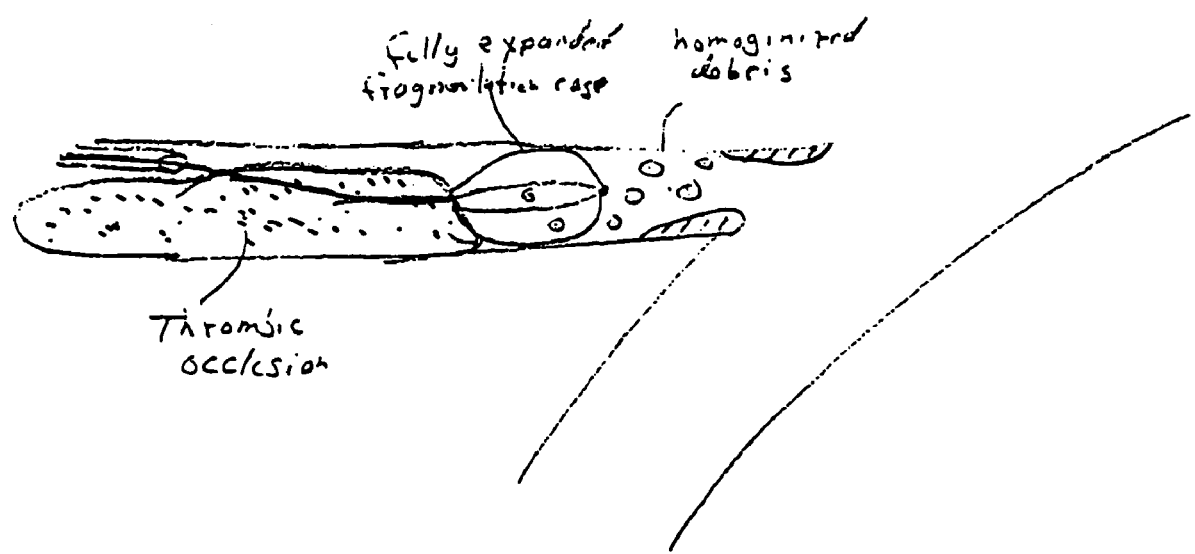

FIGS. 11A–C are anatomical views of the dialysis fistula showing another way in which the catheter system of the invention could be deployed. First, a guide wire would be inserted through a needle or through a slit into the graft and advanced to the far end of the thrombus. Then the outer sheath 36 is advanced along the guide wire to the far end of the thrombus and the guide wire is removed. Then the fragmentation catheter is advanced through the outer sheath 36 to its distal end. This process is done under fluoroscopic control.

Once in the proper position, the fragmentation catheter is deployed (see FIGS. 11B and 11C). The fragmentation cage 18 will automatically expand and match the dimensions of the inner lumen graft. The motor drive is actuated and the rotating fragmentation cage is slowly withdrawn through the clotted graft, mechanically fragmenting the clot. The fragmentation catheter may be advanced and withdrawn a second time further homogenizing the thrombotic material. After the device is withdrawn, the graft is checked for residual clot using radiographic contrast dye under fluoroscopy. The fragmentation catheter is then reintroduced as needed.

The inventor has found that rotatory of the fragmentation cage at 2000 rpm nicely fragments the thrombotic material generally smaller than 2.0 mm. Indeed, speeds of 2000 or more are generally preferred, particularly for graft clearing procedures. In that environment, speeds as high as 5500–6000 are possible and speeds of 2,000, 3,000, 3,500, 4,000, 4,500 and 5,000 rpm have been successfully tested. Balancing fragmentation, trauma and design durability, a rotary speed of 3000 rpm is currently most preferred, although other speeds can be used successfully, as noted above. The homogenized thrombolytic debris is carried safely away by the venous circulation or withdrawn as noted below. The device can homogenize blood clots and/or other obstructing material such as possibly neo-intimal hyperplasia or atheroma.

Clinical experience with an early prototype of the present invention was presented at the 1992 Radiological Society of North America Conference. The purpose of the study was to evaluate the inventive device in opening clotted arterial venous dialysis grafts percutaneously. This study confirmed the utility of the invention when the rotary basket is rotated at 2,000 r.p.m.

A further study published in Cardiovascular and Interventional Radiology (1995) was conducted to compare venous injury caused by the mechanical thrombolytic device of the invention with that of the Fogarty balloon catheter in 40 New Zealand rabbits. The study concluded that based on the rabbit model, venous injury from the device was similar to and in some cases less than that of the Fogarty balloon catheter.

A second, unpublished animal study was performed to compare the safety and efficacy of the inventive device versus pulse-spray thrombolysis. This research extensively studied the effects of the particulates on the pulmonary circulation of mongrel dogs after thrombolysis. The study included up to four repeat procedures in each dog to determine the effects of cumulative emboli. The results of the test have shown that the inventive device is significantly better than pulse-spray with regards to the number and size of emboli being sent downstream. Procedure times were also found to be shorter with the inventive device than pulse-spray. In that study, the open cage was rotated in the vessel or graft at 3,000 to 4,500 r.p.m.

Further pre-clinical in vivo testing of the inventive device has been carried out to qualify the durability of the catheter. The animal study included declotting bilateral clotted dialysis grafts in a dog model. In that study, the rotator unit was spun at 3,000 r.p.m. The results of the study show that the device is safe and effective for use in declotting thrombosed dialysis grafts.

The use of the fragmentation catheter in a retrograde fashion has been described above, but the fragmentation catheter can also homogenize thrombus when advanced forward.

As noted above, when used with a dialysis fistula the flow of blood may be clamped or otherwise reduced, or eliminated. Moreover, several passes of the rotating fragmentation cage can then be made through the thrombotic material, until it is fully homogenized, before the debris is deposited into the venous system or aspirated.

Although herein above the inventive device has been described in detail with reference to use in a dialysis fistula, it would work equally well in any vascular conduit such as a synthetic vascular graft, Hickman catheter, indwelling catheter, or peripheral graft. The device may also be used directly in natural blood vessels.

While the invention has been described in connection with what is presently considered to be the most practical and preferred embodiment, it is to be understood that the invention is not to be limited to the disclosed embodiment, but on the contrary is intended to cover various modifications and equivalent arrangements included within the spirit and scope of the appended claims.

What is claimed is:

1. A method for fragmenting thrombotic material in a vascular conduit comprising the steps of:
   (a) introducing a fragmentation catheter in the vascular conduit, wherein the fragmentation catheter comprises an expandable distal end that automatically expands to conform to the shape and diameter of the inner lumen of the vascular conduit upon deployment of the expandable distal end;
   (b) deploying the expandable distal end;
   (c) rotating the expandable distal end at a speed capable of homogenizing thrombotic material; and
   (d) withdrawing the rotating expandable distal end through thrombotic material in the vascular conduit.

2. The method of claim 1, wherein the expandable distal end includes a soft, flexible tip.

3. The method of claim 1, wherein the expandable distal end is made of spring tempered wire.

4. The method of claim 1, wherein the fragmentation catheter is coupled to a side arm for applying fluid or suction to the inner lumen of the vascular conduit.

5. The method of claim 1, wherein the fragmentation catheter is operably coupled at a proximal end portion thereof to a rotator unit for rotating the expandable distal end.

6. The method of claim 1, wherein the fragmentation catheter comprises a flexible drive shaft, where the expandable distal end is connected to a distal end of the flexible drive shaft.

7. The method of claim 1, wherein the fragmentation catheter comprises an outer sheath assembly slidably disposed on the flexible drive shaft for selectively receiving the expandable distal end therewithin, where the expandable distal end is deployed from the outer sheath assembly.

8. The method of claim 1, wherein the expandable distal end is rotated at a speed of 2000–6000 rpm.

9. The method of claim 1, wherein the expandable distal end is rotated at a speed in excess of 2000 rpm.

10. The method of claim 1, wherein the expandable distal end is rotated at a speed of 3000–4500 rpm.

11. The method of claim 1, wherein the expandable distal end is rotated at a speed of 4000 rpm.

12. The method of claim 1, wherein the speed at which the expandable distal end is rotated is controlled by a motor.

13. The method of claim 12, wherein the motor is battery operated.

14. The method of claim 1, wherein the vascular conduit is a dialysis fistulae.

15. The method of claim 1, wherein the vascular conduit is a synthetic vascular graft.

16. The method of claim 1, which further comprises checking the vascular conduit for residual thrombotic material using radiographic contrast dye under fluoroscopy.

17. The method of claim 1, wherein the fragmentation catheter comprises an outer sheath from which the expandable distal end is deployed.

18. The method of claim 17, wherein the expandable distal end is contained within the outer sheath upon introduction of the fragmentation catheter in the vascular conduit.

19. The method of claim 1, wherein a handle is attached to a proximal end of the fragmentation catheter for deploying the expandable distal end.

20. The method of claim 1, wherein the expandable distal end is advanced up to an anastomosis in step (a).

21. The method of claim 1, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, and the vascular conduit is a dialysis fistulae or a synthetic vascular graft.

22. The method of claim 1, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, the fragmentation catheter comprises a side arm for applying fluid or suction to the inner lumen of the vascular conduit, and the vascular conduit is a dialysis fistulae or a synthetic vascular graft.

23. The method of claim 1, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, the fragmentation catheter comprises a side arm for applying fluid or suction to the inner lumen of the vascular conduit, the expandable distal end comprises a soft, flexible tip at its distal end, and the vascular conduit is a dialysis fistulae or a synthetic vascular graft.

24. The method of claim 1, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, the expandable distal end is rotated at a speed in excess of 2000 rpm, and the vascular conduit is a dialysis fistulae or a synthetic vascular graft.

25. The method of claim 1, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, the expandable distal end is rotated at a speed of 3000–4500 rpm, and the vascular conduit is a dialysis fistulae or a synthetic vascular graft.

26. The method of claim 1, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, the expandable distal end is rotated at a speed of 4000 rpm, and the vascular conduit is a dialysis fistulae or a synthetic vascular graft.

27. A method for fragmenting thrombotic material in a vascular conduit comprising the steps of:
(a) introducing a fragmentation catheter in the vascular conduit, wherein the fragmentation catheter comprises an expandable distal end that automatically expands to conform to the shape and diameter of the inner lumen of the vascular conduit upon deployment of the expandable distal end;
(b) deploying the expandable distal end;
(c) rotating the expandable distal end at a speed capable of homogenizing thrombotic material; and
(d) advancing the rotating expandable distal end through thrombotic material in the vascular conduit.

28. The method of claim 27, wherein the expandable distal end includes a soft, flexible tip.

29. The method of claim 27, wherein the expandable distal end is made of spring tempered wire.

30. The method of claim 27, wherein the fragmentation catheter is coupled to a side arm for applying fluid or suction to the inner lumen of the vascular conduit.

31. The method of claim 27, wherein the fragmentation catheter is operably coupled at a proximal end portion thereof to a rotator unit for rotating the expandable distal end.

32. The method of claim 27, wherein the fragmentation catheter comprises a flexible drive shaft, where the expandable distal end is connected to a distal end of the flexible drive shaft.

33. The method of claim 27, wherein the fragmentation catheter comprises an outer sheath assembly slidably disposed on the flexible drive shaft for selectively receiving the expandable distal end therewithin, where the expandable distal end is deployed from the outer sheath assembly.

34. The method of claim 27, wherein the expandable distal end is rotated at a speed of 2000–6000 rpm.

35. The method of claim 27, wherein the expandable distal end is rotated at a speed in excess of 2000 rpm.

36. The method of claim 27, wherein the expandable distal end is rotated at a speed of 3000–4500 rpm.

37. The method of claim 27, wherein the expandable distal end is rotated at a speed of 4000 rpm.

38. The method of claim 27, wherein the speed at which the expandable distal end is rotated is controlled by a motor.

39. The method of claim 38, wherein the motor is battery operated.

40. The method of claim 27, wherein the vascular conduit is a dialysis fistulae.

41. The method of claim 27, wherein the vascular conduit is a synthetic vascular graft.

42. The method of claim 27, which further comprises checking the vascular conduit for residual thrombotic material using radiographic contrast dye under fluoroscopy.

43. The method of claim 27, wherein the fragmentation catheter comprises an outer sheath from which the expandable distal end is deployed.

44. The method of claim 43, wherein the expandable distal end is contained within the outer sheath upon introduction of the fragmentation catheter in the vascular conduit.

45. The method of claim 27, wherein a handle is attached to a proximal end of the fragmentation catheter for deploying the expandable distal end.

46. The method of claim 27, wherein the expandable distal end is advanced up to an anastomosis.

47. The method of claim 27, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, and the vascular conduit is a dialysis fistulae or a synthetic vascular graft.

48. The method of claim 27, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, the fragmentation catheter comprises a side arm for applying fluid or suction to the inner lumen of the vascular conduit, and the vascular conduit is a dialysis fistulae or a synthetic vascular graft.

49. The method of claim 27, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, the fragmentation catheter comprises a side arm for applying fluid or suction to the inner lumen of the vascular conduit, the expandable distal end comprises a soft, flexible tip at its distal end, and the vascular conduit is a dialysis fistulae or a synthetic vascular graft.

50. The method of claim 27, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, the expandable distal end is rotated at a speed in excess of 2000 rpm, and the vascular conduit is a dialysis fistulae or a synthetic vascular graft.

51. The method of claim 27, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, the expandable distal end is rotated at a speed of 3000–4500 rpm, and the vascular conduit is a dialysis fistulae or a synthetic vascular graft.

52. The method of claim 27, wherein the expandable distal end is made of memory wire, the speed at which the fragmentation member is rotated is controlled by a motor, a handle is attached to a proximal end of the fragmentation catheter for deploying the expandable distal end, the fragmentation catheter comprises an outer sheath from which the expandable distal end is deployed, the expandable distal end is contained within the outer sheath upon introduction of the fragmentation catheter in the vascular conduit, the expandable distal end is rotated at a speed of 4000 rpm, and the vascular conduit is a dialysis fistulae or a synthetic vascular graft.

* * * * *